(12) United States Patent
Yanagisawa

(10) Patent No.: US 10,551,363 B2
(45) Date of Patent: Feb. 4, 2020

(54) SYSTEM FOR MONITORING OPERATING STATUS OF CHROMATOGRAPH TO DETERMINE WHETHER THE CHROMATOGRAPH IS OPERATING NORMALLY OR ABNORMALLY

(71) Applicant: SHIMADZU CORPORATION, Kyoto-shi, Kyoto (JP)

(72) Inventor: Toshinobu Yanagisawa, Kyoto (JP)

(73) Assignee: SHIMADZU CORPORATION, Kyoto-shi (JP)

(*) Notice: Subject to any disclaimer, the term of this patent is extended or adjusted under 35 U.S.C. 154(b) by 491 days.

(21) Appl. No.: 14/625,155

(22) Filed: Feb. 18, 2015

(65) Prior Publication Data
US 2015/0233873 A1   Aug. 20, 2015

(30) Foreign Application Priority Data
Feb. 19, 2014 (JP) ................. 2014-029628

(51) Int. Cl.
G01N 30/88     (2006.01)
G01N 30/20     (2006.01)
(Continued)

(52) U.S. Cl.
CPC ............ *G01N 30/88* (2013.01); *G01N 30/20* (2013.01); *G01N 30/24* (2013.01); *G01N 30/86* (2013.01);
(Continued)

(58) Field of Classification Search
None
See application file for complete search history.

(56) References Cited

U.S. PATENT DOCUMENTS

| 5,938,817 A * | 8/1999 | Shibamoto | G01N 30/12 |
| | | | 73/23.24 |
| 2010/0116016 A1* | 5/2010 | Bungo | G01N 30/62 |
| | | | 73/1.02 |

(Continued)

FOREIGN PATENT DOCUMENTS

| JP | 11-326300 A | 11/1999 |
| JP | 2013-053868 A | 3/2013 |

OTHER PUBLICATIONS

Office Action dated Jan. 16, 2017, issued in counterpart Chinese Application No. 201510072581.4, with English translation. (8 pages).

(Continued)

*Primary Examiner* — Michael Jung
(74) *Attorney, Agent, or Firm* — Westerman, Hattori, Daniels & Adrian, LLP

(57) ABSTRACT

Provided is a system 100 for monitoring an operating status of a chromatograph to determine whether or not an abnormality due to an external condition independent of the characteristics of a sample being analyzed is present in the operating status of the chromatograph. This system includes: an external-condition measurement device (pressure sensor 19A, column oven thermometer 19B and room temperature thermometer 19C) for performing a time-series of measurement of the external condition and for obtaining a series of external-condition-related data; an index value calculator 23 for calculating an index value based on the series of the external-condition-related data obtained through an analysis; and an index value storage (data storage 24) for storing the index value for the analysis, with the index value being linked with an analysis data obtained through the analysis.

8 Claims, 5 Drawing Sheets

(51) Int. Cl.
*G01N 30/24* (2006.01)
*G01N 30/86* (2006.01)
*G01N 30/02* (2006.01)
*G01N 30/32* (2006.01)
*G01N 30/30* (2006.01)

(52) U.S. Cl.
CPC ......... *G01N 30/8658* (2013.01); *G01N 30/30* (2013.01); *G01N 30/32* (2013.01); *G01N 2030/025* (2013.01); *G01N 2030/027* (2013.01); *G01N 2030/8804* (2013.01)

(56) References Cited

U.S. PATENT DOCUMENTS

| | | | | |
|---|---|---|---|---|
| 2011/0308298 | A1* | 12/2011 | Magni | G01N 30/32 73/23.35 |
| 2012/0096919 | A1* | 4/2012 | Choikhet | G01N 30/24 73/1.02 |
| 2012/0285223 | A1* | 11/2012 | Andrews | G01N 30/8672 73/61.53 |
| 2014/0033793 | A1* | 2/2014 | Thorson | G01N 33/0006 73/1.02 |
| 2014/0067304 | A1* | 3/2014 | Sasaki | G01N 30/8658 702/89 |
| 2014/0257712 | A1* | 9/2014 | Mito | G01N 30/74 702/25 |
| 2014/0299542 | A1* | 10/2014 | Song | G01N 30/00 210/635 |
| 2015/0076068 | A1* | 3/2015 | Andrews | B01D 15/161 210/656 |
| 2015/0293064 | A1* | 10/2015 | Aota | G01N 30/34 73/61.52 |

OTHER PUBLICATIONS

Office Action dated May 3, 2016, issued in counterpart Chinese Patent Application No. 201510072581.4, with English translation. (18 pages).

Office Action dated Nov. 8, 2016, issued in counterpart Chinese Application No. 201510072581.4, with English translation. (11 pages).

* cited by examiner

SYSTEM FOR MONITORING OPERATING STATUS OF CHROMATOGRAPH TO DETERMINE WHETHER THE CHROMATOGRAPH IS OPERATING NORMALLY OR ABNORMALLY

TECHNICAL FIELD

The present invention relates to a system for monitoring an operating status of a chromatograph to determine whether or not the chromatograph is operating normally.

BACKGROUND ART

In a chromatograph (a liquid chromatograph and a gas chromatograph), if an external condition independent of the characteristics of the sample (such as the pressure of a mobile phase, the room temperature or the temperature in a column oven) changes due to some reasons during an analysis, it is impossible to correctly obtain data, such as the retention time. Therefore, in an analysis using a chromatograph, those external conditions are continuously monitored, and when a measured value is found to have deviated from a normal range, a measure is taken to prevent the analysis from being continued under abnormal conditions. Examples of the measure to be taken include alarming users by sound or light, automatically discontinuing the analysis and/or restarting the analysis after automatically resolving the abnormality (for example, see Patent Literature 1).

In recent years, new standards (guidelines) called GLP (Good Laboratory Practice) and GMP (Good Manufacturing Practice) have been introduced in some fields, such as the inspection of foodstuffs as well as the development and evaluation of new medicines, in order to ensure the reliability of the measurement results. GLP/GMP impose severe standards on the management of data which include the set conditions used in a test or inspection as well as its result, and the validity of the analyzing system used in the measurement needs to be verified. In the case of an analysis using a chromatograph, those requirements cannot be satisfied by merely preventing an analysis from being performed under abnormal conditions; it is also necessary to keep a log which proves that the analysis has been normally performed. To this end, in conventional chromatographs, the measured data of the aforementioned external conditions are saved and linked with the data obtained from a sample in each analysis as well as other items of information.

The data of the external conditions thus saved are not only available for proving that the analysis has been normally performed; those data can also be used to analyze their temporal change and prevent abnormalities from actually occurring. For example, the pressure of the mobile phase changes with the aging of the column, and therefore, the obtained pressure data shows a temporal change in which the pressure gradually changes within a normal range toward abnormal values. From this temporal change, it is possible to estimate the timing to replace the column.

CITATION LIST

Patent Literature

Patent Literature 1: JP 11-326300 A

SUMMARY OF INVENTION

Technical Problem

Since external conditions are continuously monitored during the analysis, an enormous amount of data on the external conditions are obtained. To verify the validity of the external conditions, it is necessary to extract relevant information from the huge volume of data, which consumes considerable time and labor while involving the possibility of incorrectly sorting out data. This problem similarly occurs in the case of analyzing the data to prevent abnormalities from actually occurring.

The problem to be solved by the present invention is to provide a system for monitoring an operating status of a chromatograph, the system keeping an operation log which is small in data quantity yet sufficient for proving that the chromatograph has normally operated during the analysis.

Solution to Problem

To solve the previously described problem, the present invention provides a system for monitoring an operating status of a chromatograph to determine whether or not an abnormality due to an external condition independent of the characteristics of a sample being analyzed is present in the operating status of the chromatograph, the system including:
 a) an external-condition measurement device for performing a time-series measurement of the external condition and for obtaining a series of external-condition-related data;
 b) an index value calculator for calculating an index value based on the series of the external-condition-related data obtained through an analysis; and
 c) an index value storage for storing the index value for the analysis, with the index value being linked with an analysis data obtained through the analysis.

In the system for monitoring an operating status of a chromatograph according to the present invention, an index value which is calculated based on a series of external-condition-related data obtained through an analysis is stored in the index value storage. The amount of data to be saved is smaller than in the case where the series of external-condition-related data are stored as they are.

When a plurality of analyses are performed, an index value is calculated for each of the plurality of analyses, and the index value stored in the index value storage is linked with a series of external-condition-related data of each of the plurality of analyses. Otherwise it is also possible to calculate an index value for a plurality of analyses and store it in the index value storage linking with the whole external-condition-related data of the plurality of analyses.

When a plurality of samples of the same kind are sequentially analyzed using a chromatograph, the analysis is repeatedly performed under the same conditions. In this case, the time history of the external conditions should basically be the same in every analysis as long as no abnormality is present in the system. Accordingly, when a plurality of analysis of the same condition are sequentially performed, it is possible to use, as the index value, a value obtained by comparing the external-condition-related data obtained in one analysis at a plurality of points in time from the beginning of the analysis and the external-condition-related data obtained in another analysis immediately preceding the analysis at the corresponding plurality of points in time from the beginning of the analysis. For example, when $P_n(t_i)=P_n(t_1), P_n(t_2), \ldots, P_n(t_N)$ denote values of an external-condition-related data respectively obtained in the nth analysis at N points in time $t_i=t_1, t_2, \ldots, t_N$ from the beginning of the analysis while $P_{n-1}(t_i)=P_{n-1}(t_1), P_{n-1}(t_2), \ldots, P_{n-1}(t_N)$ denote values of the external-condition-related data respectively obtained in the immediately preceding (n−1)th analysis, one or more of the following three values can be used as the index value or values:
(i) Maximum difference: $R_n = |P_n(t_{max}) - P_{n-1}(t_{max})|$, where $t_{max}$ is the point in time where $|P_n(t_i) - P_{n-1}(t_i)|$ is maximized (ii) Average difference $x_n = \frac{1}{N} \sum_{i=1}^{N} |P_n(t_i) - P_{n-1}(t_i)|$ (iii) Degree of similarity $S_n = \dfrac{\sum_{i=1}^{N} P_n(t_i) \cdot P_{n-1}(t_i)}{\sqrt{\sum_{i=1}^{N} P_n^2(t_i)} \cdot \sqrt{\sum_{i=1}^{N} P_{n-1}^2(t_i)}}$ It should be noted that the average difference is hereinafter denoted as "$x_n$."

In the calculation of the aforementioned index value, it is possible to use, instead of $P_{n-1}(t_i)$, an average $P_{n-1,m}(t_i)$ value of the external-condition-related data obtained through m analyses (where m is a natural number, including one) from the (n−m)th through (n−1)th analyses. Such an average value $P_{n-1,m}(t_i)$ can be expressed as follows:

$$P_{n-1,m}(t_i) = \frac{1}{m} \sum_{j=n-m}^{n-1} P_j(t_i)$$

The external-condition-related data may be one or more parameters selected from the group of the pressure of a mobile phase, the flow rate of the mobile phase, the room temperature, and the temperature of a column oven.

The system for monitoring an operating status of a chromatograph according to the present invention may additionally include an index-value abnormality handler for taking a predetermined measure when the index value is within a predetermined range of abnormal values or when the index value is out of a predetermined range of normal values. For example, the predetermined measure may be the operation of generating a warning signal, discontinuing the analysis and/or executing a measure for resolving the abnormality (e.g. as described in Patent Literature 1).

Advantageous Effects of the Invention

In the system for monitoring an operating status of a chromatograph according to the present invention, an index value which is calculated based on a series of external-condition-related data is stored in the index value storage. The amount of data to be saved for proving that the chromatograph has normally operated during the analysis is smaller than in the case where the values of the external-condition-related data are stored as they are. Therefore, it is easier to verify the validity of external-conditions or perform a data analysis for preventing abnormalities from actually occurring.

DESCRIPTION OF EMBODIMENTS

One embodiment of the system for monitoring an operating status of a chromatograph according to the present invention is hereinafter described using FIGS. 1-5.

Figure 1:
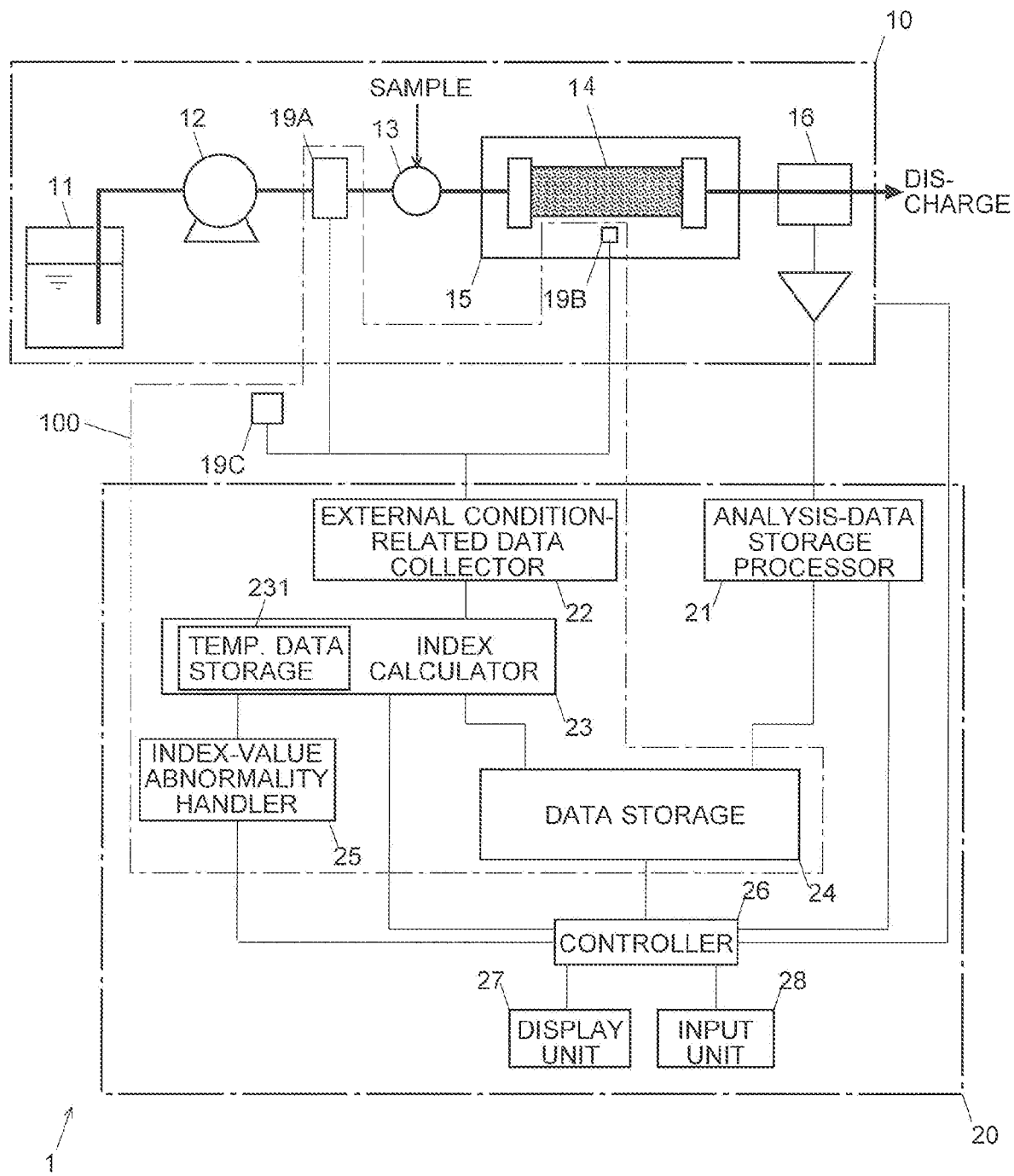
FIG. 1 is a schematic configuration diagram of a liquid chromatograph using one embodiment of the system for monitoring an operating status of a chromatograph according to the present invention.

FIG. 1 is a schematic configuration diagram of a liquid chromatograph 1 including a system for monitoring an operating status of a chromatograph of the present embodiment. The liquid chromatograph 1 has an analyzer unit 10 and a data processor unit 20. The analyzer unit 10 includes a mobile phase container 11, a liquid-sending pump 12, an auto-injector 13, a column 14, a column oven 15 and a detector 16. The mobile phase container 11 holds a mobile phase, which is pumped by the liquid-sending pump 12 and made to sequentially pass through the auto-injector 13, the column 14 and the detector 16. The column 14 is contained in the column oven 15 and is maintained at a constant temperature as long as the column oven 15 is normally operating. The detector 16 detects each individual component which has passed through the column 14, and its detection signal is sent to the data processor unit 20 as analysis data. The detector 16 is a spectrophotometer, whose configuration will not be described in detail since spectrophotometers are widely used in common liquid chromatographs.

A pressure sensor 19A for measuring the pressure of the mobile phase is provided in the passage between the liquid-sending pump 12 and the auto-injector 13. A column oven thermometer 19B for measuring the temperature inside the column oven 15 is provided in this oven. A room temperature thermometer 19C for measuring the room temperature is provided outside the analyzer unit 10.

The data processor unit 20 includes an analysis-data storage processor 21 for performing processes related to the analysis data, an external-condition-related data collector and an index value calculator 23 for performing processes based on external-condition-related data, as well as a data storage 24 for holding the analysis data processed by the analysis-data storage processor 21 and the index values calculated by the index value calculator 23. The analysis-data storage processor 21 processes detection signals of the detector 16 in a manner to be described later and saves the obtained data in the data storage 24. The external-condition-related data collector 22 collects external-condition-related data obtained through the pressure sensor 19A, the column oven thermometer 19B and the room temperature thermometer 19C and sends those data to the index value calculator 23. The index value calculator 23 processes the external-condition-related data in a manner to be described later to calculate an index value. The index value calculator 23 is provided with a temporary data storage 231 for temporarily holding data to be used in the calculation of the index value.

The data processor unit 20 is provided with an index-value abnormality handler 25. The index-value abnormality handler 25 receives an index value calculated by the index value calculator 23 and generates a warning sound if the index value is within a predetermined range of abnormal values or when the index value is out of a predetermined range of normal values. In addition to or instead of generating the warning sound, it is also possible to turn on a warning lamp or display information notifying users of an occurrence of an abnormality on a display unit 27 (which will be mentioned later). It is also possible to discontinue the analysis in addition to or instead of generating those warning signals.

In addition to the previously described components, the data processor unit 20 has a controller 26 for controlling the other components and the liquid chromatograph 1, a display unit 27 as well as an input unit 28 including a keyboard, mouse and other devices.

In the previously described configuration, the following components constitute the system 100 for monitoring an operating status of the chromatograph: the pressure sensor 19A, the column oven thermometer 19B and the room temperature thermometer 19C (each of which corresponds the external-condition measurement device in the present invention), the external-condition-related data collector 22 and the index value calculator 23 (which correspond to the index value calculator in the present invention), the data storage 24 (which corresponds to the index value storage in the present invention), as well as the index-value abnormality handler 25.

An operation of the liquid chromatograph 1 is hereinafter described. In the following description, it is assumed that there are a total of $n_{max}$ samples and those samples are sequentially subjected to an analysis.

While the mobile phase in the mobile phase container 11 is continuously supplied into the auto-injector 13 by the liquid-sending pump 12, the auto-injector 13 injects a sample into the mobile phase. The sample injection is performed $n_{max}$ times at preset intervals of time which are adequately longer than the period of time required for all the components of one sample to pass through the column 14. Thus, for each sample injected, the components are temporally separated while passing through the column 14, and the detector 16 produces an analysis-data signal whose intensity changes with time. In the present embodiment, since a spectrophotometer is used as the detector 16, the analysis data obtained at each point in time (retention time) consist of a large number of analogue signals forming a spectrum over a range of wavelengths, with each signal obtained at one wavelength. Those analogue signals are sent to the analysis-data storage processor 21. The analysis-data storage processor 21 converts the analogue signals in the spectrum into digital signals representing numerical values. Eventually, for each sample, the identification information of the sample, the retention times, and the numerical data of the spectrum obtained at each retention time are stored in the data storage 24.

While the analysis data are being obtained through the detector 16 in the previously described way, the external-condition-related data, i.e. the pressure of the mobile phase, the temperature inside the column oven and the room temperature are respectively measured with the pressure sensor 19A, the column oven thermometer 19B and the room temperature thermometer 19C. Those external-condition-related data are transmitted N times to the external-condition-related data collector 22 at preset intervals of time within every analysis of one sample. As a result, for an analysis of an nth sample injected from the auto-injector 13 (this analysis is hereinafter called the "nth analysis", where $1 \leq n \leq n_{max}$), the external-condition-related data of the pressure $P_n(t_i)$, the temperature $Tc_n(t_i)$ inside the column oven and the room temperature $Tr_n(t_i)$, are obtained N times, at $t_i = t_1, t_2, \ldots$ and $t_N$, in the external-condition-related data collector 22 as follows:

$$P_n(t_i) = P_n(t_1), P_n(t_2), \ldots, P_n(t_N)$$

$$Tc_n(t_i) = Tc_n(t_1), Tc_n(t_2), \ldots, Tc_n(t_N)$$

$$Tr_n(t_i) = Tr_n(t_1), Tr_n(t_2), \ldots, Tr_n(t_N)$$

Based on the external-condition-related data thus obtained, the index value calculator 23 calculates an index value for the nth analysis in a manner to be described later. In the calculation of the index value, the external-condition-related data obtained in the last m analyses preceding the nth analysis are used, which are temporarily held in the temporary data storage 231. Each set of the temporarily stored data of the index value are either erased or overwritten with newly obtained external-condition-related data after the completion of an analysis which is m cycles later than the analysis in which the data concerned were obtained. Although the following description is focused on a method of calculating an index value based on the pressure $P_n(t_i)$, the description similarly applies to the case of the temperature $Tc_n(t_i)$ inside the column oven or the room temperature $Tr_n(t_i)$.

Figure 2:
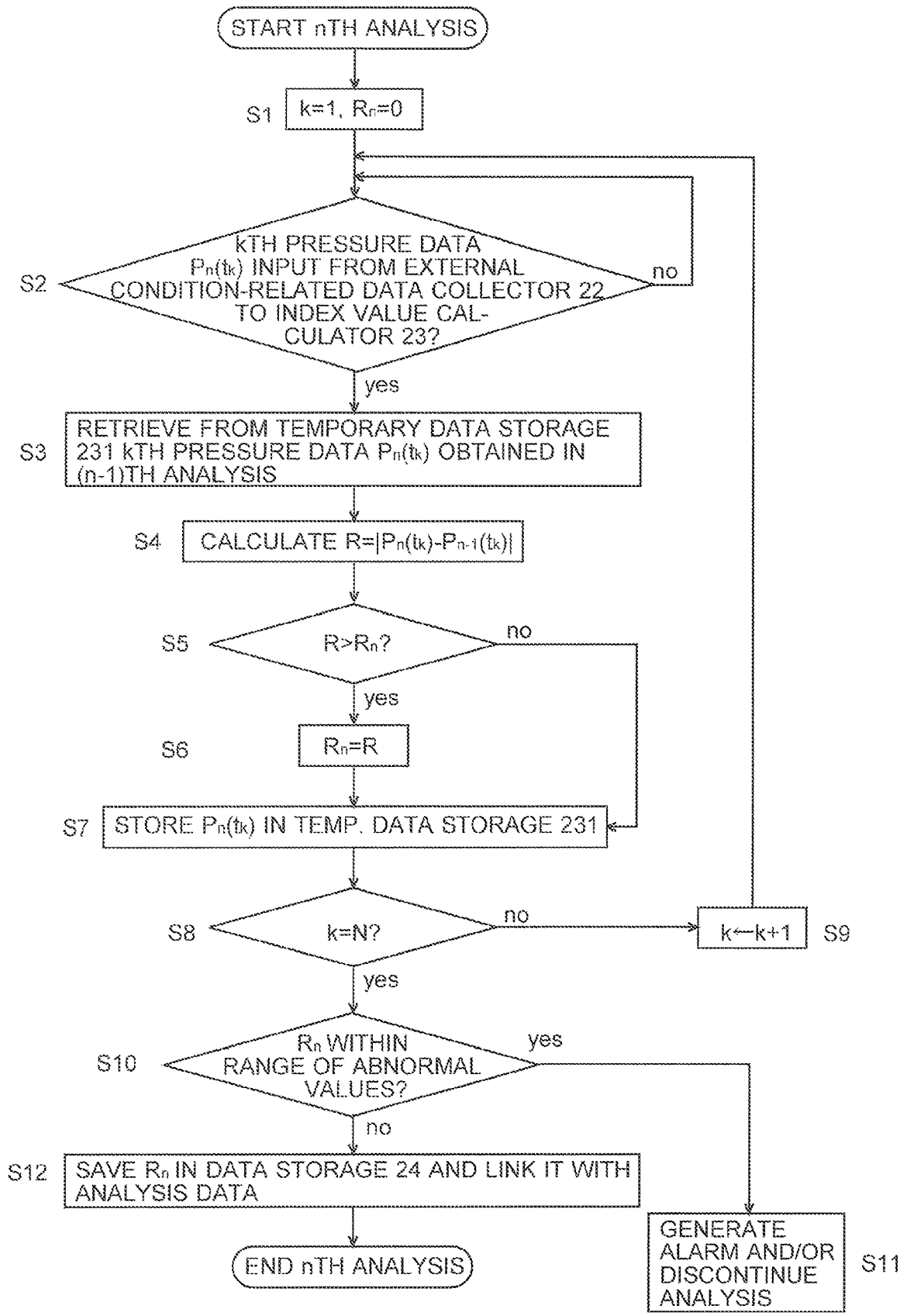
FIG. 2 is a flowchart showing a process of calculating and storing the maximum difference $R_n$ in the value of an external-condition-related data in the system for monitoring an operating status of a chromatograph of the present embodiment.

(i) Calculation of Maximum Difference $R_n$ of External-Condition-Related Data (Flowchart in FIG. 2)

First, when the nth analysis is initiated, the index value calculator 23 sets k=1 and $R_n$=0 as the initial values (Step S1), where k is the order of the pressure data $P_n(t_i)$ obtained in the nth analysis. Next, the index value calculator 23 waits for an input of the pressure data $P_n(t_k)$ from the external-condition-related data collector 22 (Step S2). After the data is input, the process goes to Step S3.

In the temporary data storage 231, the values of the pressure $P_{n-1}(t_i) = P_{n-1}(t_1), P_{n-1}(t_2), \ldots, P_{n-1}(t_N)$ obtained in the previous analysis, or the (n−1)th analysis, are stored. In Step S3, the index value calculator 23 retrieves from the temporary data storage 231 the kth pressure data $P_{n-1}(t_k)$ in the (n−1)th analysis (the first pressure data when the aforementioned initial values are set). Then, the index value calculator 23 calculates $R = |P_n(t_k) - P_{n-1}(t_k)|$ (Step S4). If the value of R is found to be greater than the current value of $R_n$ (Step S5), the value of $R_n$ is replaced by the presently obtained value of R (Step S6).

Besides, the index value calculator 23 stores the value of $P_n(t_k)$ in the temporary data storage 231 (Step S7). This operation can be performed at any stage after the value of NO is obtained in Step S2. The value of $P_n(t_k)$ thus stored in the temporary data storage 231 will be used in the calculation of the index value in the (n+1)th analysis. The processes for $P_n(t_k)$ are completed at this point.

Subsequently, if the value of k is found to be less than N in Step S8, the value of k is increased by one (Step S9) and the operation returns to Step S2 to perform the processes of Steps S2 through S7 for $P_n(t_{k-1})$. On the other hand, if the value of k is found to have reached N in Step S8, the value of $R_n$ at this point is adopted as the "maximum difference $R_n$", i.e. the index value in the nth analysis. The index-value abnormality handler 25 determines whether or not $R_n$ is within the range of abnormal values (Step S10). If $R_n$ is found to be within that range, the system generates a warning signal and/or discontinues the analysis (Step S11). If $R_n$ is not within the range of abnormal values, the index value calculator 23 stores the value of $R_n$ in the data storage 24 and links this value with the analysis data obtained in the nth analysis (Step S12). Thus, the sequence of the processes in the nth analysis is completed.

In the previous example, $R=|P_n(t_k)-P_{n-1}(t_k)|$ is calculated every time a new pressure data $P_n(t_k)$ is input from the external-condition-related data collector 22. It is also possible to calculate $R=|P_n(t_i)-P_{n-1}(t_i)|$ for each data $P_n(t_i)$ after the entire set of the pressure data $P_n(t_i)=P_n(t_1), P_n(t_2), \ldots, P_n(t_N)$ are input, and to adopt the largest value of R as the maximum difference $R_n$.

Figure 3:
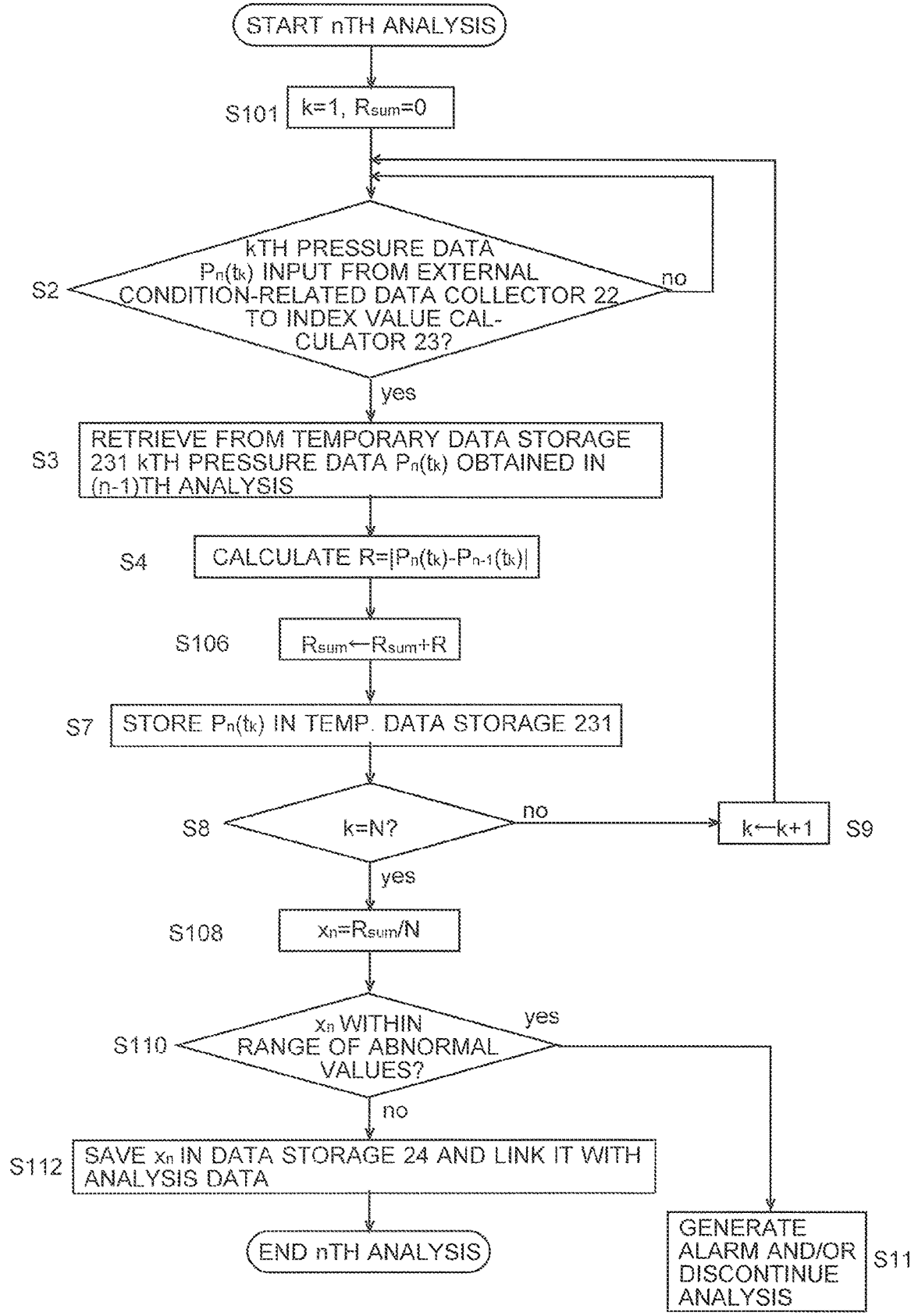
FIG. 3 is a flowchart showing a process of calculating and storing an average difference $x_n$ of the value of an external-condition-related data in the system for monitoring an operating status of a chromatograph of the present embodiment.

(ii) Calculation of Average Difference $x_n$ of External-Condition-Related Data (Flowchart in FIG. 3)

The calculation of an average difference $x_n$ of the external-condition-related data includes some operations common to the calculation of the maximum difference Such common operations will not be fully described but merely mentioned as such. Initially, the index value calculator 23 sets k=1 and $R_{sum}=0$ as the initial values (Step S101), where $R_{sum}$ is the sum of the first through kth values of R. Subsequently, the operations of Steps S2 through S4 are performed in the previously described way, after which the process goes to Step S106. In Step S106, the value of R obtained for i=k in Step S4 is added to $R_{sum}$ to obtain a new value of $R_{sum}$. The operations of Steps S7 through S9 are performed in the previously described way. If k is found to have reached N in Step S8, it means that the operational sequence of Steps S2-S4, S106 and S7 has been repeated N times. Then, in Step S108, the average difference $x_n$ is calculated by dividing $R_{sum}$ by N:

$$x_n = \frac{R_{sum}}{N} = \frac{1}{N}\sum_{i=1}^{N}|P_n(t_i)-P_{n-1}(t_i)|$$

Subsequently, the index-value abnormality handler 25 determines whether or not $x_n$ is within a preset range of abnormal values (Step S110) and takes the aforementioned measures if $x_n$ is found to be within that range (Step S11). If $x_n$ is not within the range of abnormal values, the index value calculator 23 stores the value of $x_n$ in the data storage 24 and links this value with the analysis data obtained in the nth analysis (Step S112). Thus, the sequence of the processes in the nth analysis is completed.

Figure 4:
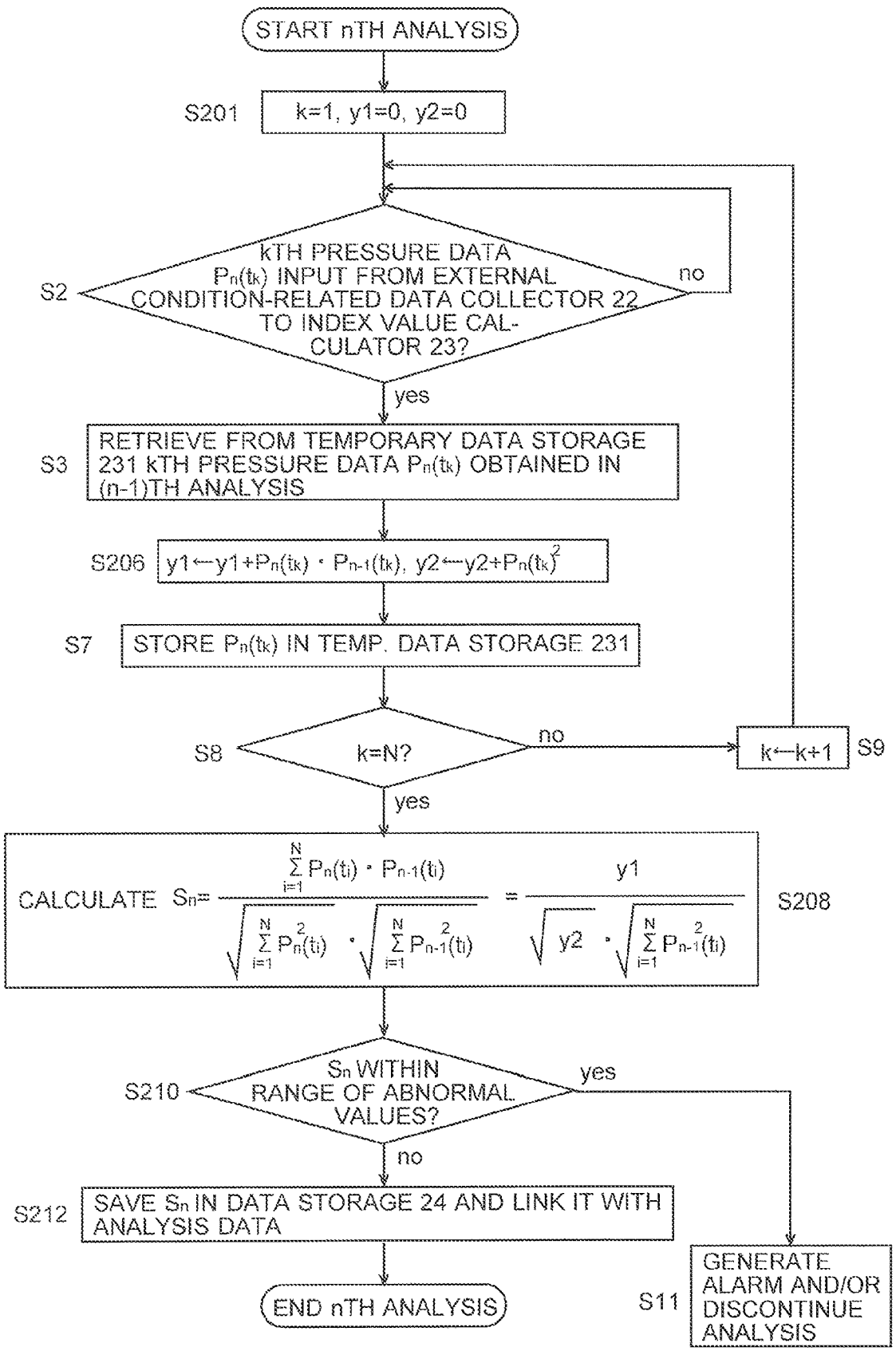
FIG. 4 is a flowchart showing a process of calculating and storing the degree of similarity $S_n$ of an external-condition-related data in the system for monitoring an operating status of a chromatograph of the present embodiment.

(iii) Calculation of Degree of Similarity of External-Condition-Related Data (Flowchart in FIG. 4)

The calculation of a degree of similarity $S_n$ of the external-condition-related data also include some operations common to the calculation of the maximum difference $R_n$. Such common operations will not be fully described but merely mentioned as such. Initially, the index value calculator 23 sets k=1, y1=0 and y2=0 as the initial values (Step S201). The meaning of y1 and y2 will be explained later. In Steps S2 and S3, the same operations as in the calculation of the maximum difference $R_n$ are performed, after which the process goes to Step S206. In Step S206, $P_n(t_k)\cdot P_{n-1}(t_k)$ is added to the value of y1 which has been obtained in the (k−1)th cycle, whereby the value of y1 is replaced by the value of $\{y1+P_n(t_k)\cdot P_{n-1}(t_k)\}$. Similarly, the value of y2 is replaced by $\{y2+P_n^2(t_k)\}$. In Steps S7 through S9, the same operations as in the calculation of the maximum difference $R_n$ are performed. If k is found to have reached N in Step S8, it means that the operational sequence of Steps S2, S3, S206 and S7 has been repeated N times. As a result, the following values of y1 and y2 are obtained in Step S206:

$$y1 = \sum_{i=1}^{N} P_n(t_i) \cdot P_{n-1}(t_i)$$

$$y2 = \sum_{i=1}^{N} P_n^2(t_i)$$

Next, in Step S208, the degree of similarity $S_n$ is calculated using y1 and y2 as follows:

$$S_n = \frac{\sum_{i=1}^{N} P_n(t_i)\cdot P_{n-1}(t_i)}{\sqrt{\sum_{i=1}^{N} P_n^2(t_i)}\cdot\sqrt{\sum_{i=1}^{N} P_{n-1}^2(t_i)}} = \frac{y1}{\sqrt{y2}\cdot\sqrt{\sum_{i=1}^{N} P_{n-1}^2(t_i)}}$$

In this equation, the sum of $P_{n-1}^2(t_i)$ for i=1 to N in the denominator is calculated using the values of $P_{n-1}(t_i)$ stored in the temporary data storage 231.

Subsequently, the index-value abnormality handler 25 determines whether or not $S_n$ is within a preset range of abnormal values (Step S210) and takes the aforementioned measures if $R_n$ is found to be within that range (Step S11). If $R_n$ is not within the range of abnormal values, the index value calculator 23 stores the value of $S_n$ in the data storage 24 and links this value with the analysis data obtained in the nth analysis (Step S212). Thus, the sequence of the processes in the nth analysis is completed.

Figure 5:
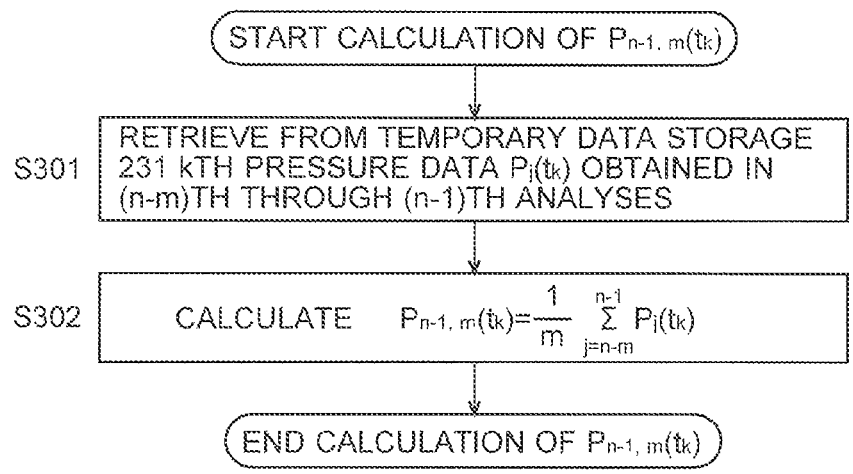
FIG. 5 is a flowchart showing a process of calculating an average $P_{n-1,m}(t_i)$ of the value of an external-condition-related data over m analyses in the system for monitoring an operating status of a chromatograph of the present embodiment.

(iv) Calculation of Average Value $P_{n-1,m}(t_k)$ of External-Condition-Related Data Through m Analyses (Flowchart in FIG. 5)

The operation of calculating the average value $P_{n-1,m}(t_k)$ is hereinafter described using FIG. 5. The calculation of the index value using the average value $P_{n-1,m}(t_k)$ can be achieved by replacing $P_{n-1}(t_k)$ with $P_{n-1,m}(t_k)$ in Step S3 in the previously described cases (i)-(iii) (FIGS. 2-4). Therefore, the following description only deals with the operation of calculating $P_{n-1,m}(t_k)$. Initially, the kth pressure data obtained in each of the (n−m)th through (n−1)th analyses is retrieved from the temporary data storage 231 (Step S301).

Then, in Step S302, $P_{n-1,m}(t_k)$ is calculated as follows:

$$P_{n-1,m}(t_k) = \frac{1}{m}\sum_{j=n-m}^{n-1} P_j(t_k)$$

Using $P_{n-1,m}(t_k)$ thus calculated in place of $P_{n-1}(t_k)$, the maximum difference $R_n$, the average difference $x_n$ or the degree of similarity $S_n$ is calculated according to the process steps described in (i)-(iii) (FIGS. 2-4). Thus, the sequence of the processes in the nth analysis is completed.

In the previously describes manner, the maximum difference $R_n$, the average difference $x_n$ and the degree of similarity $S_n$ of the external-condition-related data, as well as these index values calculated in the nth analysis using the average values $P_{n-1,m}(t_k)$ of the external-condition-related data obtained through m analyses, are linked with the data obtained in the nth analysis and stored in the data storage 24. Those index values do not only serve to prove that the nth analysis was normally performed but is also available as the data for predicting future occurrence of an abnormality due to the aging of the column or other factors.

In the previous descriptions, the operations of calculating the three index values (i)-(iii) are separately explained. In practice, the three index values can be concurrently calculated. A specific example is as follows: Initially, Steps S1, S101 and S201 for setting the initial values are concurrently performed, after which Steps S2 and S3 common to (i)-(iii) are performed. Subsequently, Step S4 which is common to the two cases (i) and (ii) is performed, while the operation in (iii) is temporarily halted. After Step S5 is performed in (i), Steps S6, S106 and S206 are concurrently performed. Then, Steps S7-S9 which are common to (i)-(iii) are performed. After Steps S108 and S208 are respectively performed in (ii) and (iii), Steps S10, S110 and S210 are concurrently performed. Step S11, which is common to (i)-(iii), may also be performed if necessary. Eventually, Steps S12, S112 and S212 are concurrently performed.

The present invention is not limited to the previous embodiment.

For example, it is possible to calculate and save only one or two of the three aforementioned kinds of index values instead of calculating and saving all the three kinds of index values as in the previous embodiment. A flow rate of the mobile phase may be measured with a flowmeter as an external condition in place of the pressure of the mobile phase measured with the pressure sensor 19A in the previous embodiment.

The index-value abnormality handler 25 provided in the previous embodiment is not indispensable to the present invention.

The system for monitoring an operating status of a chromatograph cannot only be included in a liquid chromatograph as in the previous embodiment but also may be included in a gas chromatograph.

REFERENCE SIGNS LIST

1 . . . Liquid Chromatograph
100 . . . System for Monitoring Operating Status of Chromatograph
10 . . . Analyzer Unit
11 . . . Mobile Phase Container
12 . . . Liquid-Sending Pump
13 . . . Auto-Injector
14 . . . Column
15 . . . Column Oven
16 . . . Detector
19A . . . Pressure Sensor
19B . . . Column Oven Thermometer
19C . . . Room Temperature Thermometer
20 . . . Data Processor Unit
21 . . . Analysis-Data Storage Processor
22 . . . External-Condition-Related Data Collector
23 . . . Index Value Calculator
231 . . . Temporary Data Storage
24 . . . Data Storage
25 . . . Index-Value Abnormality Handler
26 . . . Controller
27 . . . Display Unit
28 . . . Input Unit

The invention claimed is:

1. A system comprising:
a chromatograph; and
a monitoring system for monitoring an operating status of the chromatograph including:
an external-condition measurement device including a pressure sensor, a column oven thermometer, or a room temperature thermometer, the external-condition measurement device being configured to obtain a series of external-condition-related data which is one or more parameters selected from a group of a pressure of a mobile phase, a flow rate of a mobile phase, a room temperature and a temperature of a column oven;
a processor;
a computer-readable memory; and
a computer program instruction on the computer-readable medium, wherein the computer program instruction when executed by the processor calculates an index value based on the series of external-condition-related data obtained through an analysis when a plurality of analyses of a same condition are sequentially performed, wherein the index value is a value obtained by comparing the external-condition-related data obtained in one analysis at a plurality of points in time from the beginning of the analysis and the external-condition-related data obtained in another analysis immediately preceding the analysis at the corresponding plurality of points in time from the beginning of the analysis, and whose amount of data is smaller than that of the series of external-condition-related data, and stores the index value for the analysis, with the index value being linked with an analysis data obtained through the analysis.

2. The system according to claim 1, wherein one or more following three values are used as the index value or values:

(i) Maximum difference: $R_n = |P_n(t_{max}) - P_{n-1}(t_{max})|$, where $t_{max}$ is a point in time where $|P_n(t_i) - P_{n-1}(t_i)|$ is maximized (ii) Average difference: $Xn = \dfrac{1}{N} \sum_{i=1}^{N} |(P_n(t_i) - P_{n-1}(t_i)|$ (iii) Degree of similarity: $Sn = \dfrac{\sum_{i=1}^{N} (P_n(t_i) \cdot P_{n-1}(t_i))}{\sqrt{\sum_{i=1}^{N} P_n^2(t_i)} \cdot \sqrt{\sum_{i=1}^{N} P_{n-1}^2(t_i)}}$ where $P_n(t_i) = P_n(t_1), P_n(t_2), \ldots P_n(t_N)$ denote values of an external-condition-related data respectively obtained in the nth analysis at N points in time $t_i = t_1, t_2, \ldots, t_N$ from the beginning of the analysis while $P_{n-1}(t_i) = P_{n-1}(t_1), P_{n-1}(t_2), \ldots, P_{n-1}(t_N)$ denote values of the external-condition related data respectively obtained in the immediately preceding (n−1)th analysis.

3. The system according to claim 2, wherein the index value or values are obtained using, instead of $P_{n-1}(t_i)$, an average $P_{n-1,m}(t_i)$ of the values of the external-condition-related data obtained through m analyses (where m is a natural number, including one) from (n−m)th through (n−1)th analyses, where $P_{n-1,m}(t_i)$ is given by:

$$P_{n-1,m}(t_i) = \dfrac{1}{m} \sum_{j=n-m}^{n-1} P_j(t_i).$$

4. The system according to claim 3, wherein the computer program instruction when executed by the processor takes a predetermined measure when the index value is within a predetermined range of abnormal values or when the index value is out of a predetermined range of normal values.

5. The system according to claim 2, wherein the computer program instruction when executed by the processor takes a predetermined measure when the index value is within a predetermined range of abnormal values or when the index value is out of a predetermined range of normal values.

6. The system according to claim 1, wherein the computer program instruction when executed by the processor takes a predetermined measure when the index value is within a predetermined range of abnormal values or when the index value is out of a predetermined range of normal values.

7. The system according to claim 1, wherein when a plurality of analyses are performed, the computer program instruction when executed by the processor calculates an index value for each of the plurality of analyses, and the computer-readable memory stores the index values for the plurality of analyses, with each of the index values being linked with each of a plurality of series of external-condition-related data of the plurality of analyses.

8. The system according to claim 1, wherein when a plurality of analyses are performed, the computer program instruction when executed by the processor calculates an index value for the plurality of analyses, and the computer-readable memory stores the index value for the plurality of analyses, with the index values being linked with a plurality of series of external-condition-related data of the plurality of analyses.

* * * * *